US010786209B2

(12) United States Patent
Park et al.

(10) Patent No.: US 10,786,209 B2
(45) Date of Patent: Sep. 29, 2020

(54) MONITORING SYSTEM FOR STROKE (71) Applicant: KOREA RESEARCH INSTITUTE OF STANDARDS AND SCIENCE, Daejeon (KR)

(72) Inventors: Se Jin Park, Anseong-si (KR); Seung hee Hong, Daejeon (KR); Da Mee Kim, Daejeon (KR)

(73) Assignee: KOREA RESEARCH INSTITUTE OF STANDARDS AND SCIENCE, Daejeon (KR)

( * ) Notice: Subject to any disclaimer, the term of this patent is extended or adjusted under 35 U.S.C. 154(b) by 163 days.

(21) Appl. No.: 15/943,524

(22) Filed: Apr. 2, 2018

(65) Prior Publication Data

US 2018/0279966 A1    Oct. 4, 2018

(30) Foreign Application Priority Data

Mar. 31, 2017    (KR) .................. 10-2017-0041644

(51) Int. Cl.
*A61B 5/00*    (2006.01)
*A61B 5/0488*    (2006.01)
*A61B 5/0496*    (2006.01)
*A61B 5/0484*    (2006.01)
*A61B 5/16*    (2006.01)
(Continued)

(52) U.S. Cl.
CPC .......... *A61B 5/7282* (2013.01); *A61B 5/0006* (2013.01); *A61B 5/02055* (2013.01); *A61B 5/0476* (2013.01); *A61B 5/0484* (2013.01); *A61B 5/0488* (2013.01); *A61B 5/0496* (2013.01); *A61B 5/165* (2013.01); *A61B 5/18* (2013.01); *A61B 5/4094* (2013.01); *A61B 5/7405* (2013.01); *A61B 5/021* (2013.01);
(Continued)

(58) Field of Classification Search
CPC ..... A61B 5/7282; A61B 5/4094; A61B 5/165; A61B 5/7405; A61B 5/02055; A61B 5/18; A61B 5/0006; A61B 5/0484; A61B 5/0496; A61B 5/0488; A61B 5/0476; A61B 5/11; A61B 5/0531; A61B 5/021; A61B 5/024
See application file for complete search history.

(56) References Cited

U.S. PATENT DOCUMENTS

2011/0245707 A1*    10/2011    Castle .................. A61B 5/4094
                                                              600/544
2016/0287127 A1*    10/2016    Kesinger .............. A61B 5/4064

FOREIGN PATENT DOCUMENTS

JP    2014-527219 A    10/2014
KR    10-2011-0052783 A    5/2011
(Continued)

OTHER PUBLICATIONS

Office Action of corresponding Korean Patent Application No. 10-2017-0041644—4 pages (dated Oct. 4, 2018).
(Continued)

*Primary Examiner* — Mark Bockelman
(74) *Attorney, Agent, or Firm* — Knobbe Martens Olson & Bear LLP (57) ABSTRACT

Provided is a stroke monitoring system capable of measuring a user's biometric signal including an electroencephalogram using a device such as a wearable device for determining whether a user has a stroke for 24 hours, building a database of the measured user's biometric signal and other information, and predicting an occurrence of a user's stroke.

5 Claims, 6 Drawing Sheets

(51) Int. Cl.
*A61B 5/18* (2006.01)
*A61B 5/0205* (2006.01)
*A61B 5/0476* (2006.01)
A61B 5/024 (2006.01)
A61B 5/021 (2006.01)
A61B 5/053 (2006.01)
A61B 5/11 (2006.01)

(52) U.S. Cl.
CPC .............. *A61B 5/024* (2013.01); *A61B 5/0531* (2013.01); *A61B 5/11* (2013.01)

(56) References Cited

FOREIGN PATENT DOCUMENTS

| | | |
|---|---|---|
| KR | 10-2015-0130116 A | 11/2015 |
| KR | 10-2016-0139612 A | 12/2016 |

OTHER PUBLICATIONS

Office Action of corresponding Japanese Patent Application No. 2018-064353—5 pages (dated Feb. 27, 2019).

\* cited by examiner

MONITORING SYSTEM FOR STROKE

CROSS-REFERENCE TO RELATED APPLICATIONS

This application claims priority under 35 U.S.C. § 119 to Korean Patent Application No. 10-2017-0041644, filed on Mar. 31, 2017, in the Korean Intellectual Property Office, the disclosure of which is incorporated herein by reference in its entirety.

TECHNICAL FIELD

The following disclosure relates to a stroke monitoring system, and more particularly, to a stroke monitoring system capable of measuring a user's biometric signal including an electroencephalogram using a device such as a wearable device for determining whether a user has a stroke for 24 hours, building a database of the measured user's biometric signal and other information, and predicting an occurrence of a user's stroke.

BACKGROUND

A stroke is collectively referred to as a symptom of local neurological deficit which is suddenly caused by cerebral blood flow abnormality. The stroke may arise from a variety of causes, and is a symptom that may arise throughout all ages, but usually arises in old age.

A brain is a considerably vulnerable organ to symptoms such as a stroke. If a blood supply is blocked for 30 seconds, tissues are in an ischemic state and thus a metabolic process begins to be abnormal, if the blood supply stops for 1 minute, a brain cell function is paralyzed, and if the blood supply stops for 5 minutes, an irreversible change arises and thus necrosis of nervous cells occurs. Therefore, there was a need to prevent such a stroke and do urgent treatment when the stroke occurs.

Korean Patent Laid-Open Publication No. 10-2015-0130116 ("Apparatus and Method for Determining Stroke During Sleep", Nov. 23, 2015, hereinafter referred to as Related Art 1) discloses an apparatus for determining whether or not a user has a stroke during sleep. The method of the related art 1 will be briefly described. The related art 1 relates to a method for determining whether a user has a stroke based on a user's motion data by disposing an apparatus for determining a stroke on a user's body part, and has reliability lower than that of the method based on a user's biometric signal. There is a problem in that the method needs to perform a separate complicated process in order to increase the reliability and is limited as determining whether or not the stroke arises during user's sleep.

RELATED ART DOCUMENT

Korean Patent Laid-Open Publication No. 10-2015-0130116 ("Apparatus and Method for Determining Stroke During Sleep", Nov. 23, 2015).

The disclosure of this section is to provide background of the invention. Applicant notes that this section may contain information available before this application. However, by providing this section, Applicant does not admit that any information contained in this section constitutes prior art.

SUMMARY

An embodiment of the present invention is directed to providing a stroke monitoring system capable of determining whether a user has a stroke throughout daily life and predicting whether or not a user has a stroke or an occurrence of a user's stroke based on a user's biometric signal.

In one general aspect, a stroke monitoring system includes: a database 100 configured to store user's health information; a measurement unit 200 configured to be attached to a user or installed in a specific place to measure a biometric signal including an electroencephalogram and store the measured electroencephalogram in the database 100; a stroke determination unit 300 configured to calculate a reference range of the user's biometric signal based on the health information pre-stored in the database 100 and compare and analyze the biometric signal measured by the measurement unit 200 with the reference range to predict the occurrence of the user's stroke; a notification unit 400 configured to notify a user or a designated place when the stroke determination unit 300 determines the occurrence of the stroke or predicts the occurrence of the stroke; and a stroke history storage unit 500 configured to store the prediction history of the stroke determined by the stroke determination unit 300.

The stroke determination unit 300 may calculate the reference range based on the history and user's health information pre-stored in the database when the history is stored in the stroke history storage unit 500.

The user's health information may include a medical checkup history, medical checkup information, and user's measurement electroencephalogram information.

The measurement unit 200 may further measure one or more selected from an electromyogram, electrooculogram, a heart rate, a blood pressure, a body temperature, skin conductivity, and a movement of a body.

The measurement unit 200 may measure other types of biometric signals according to a user's state.

The user's state may be states in which the user is exercising, sleeping, driving, or is in other daily lives.

The measurement unit 200 may communicate with a signal device 210 installed at other locations according to the user's state to check the user's state.

The reference range may be changed according to the user's state.

The notification unit 400 may output a notification sound to allow a user to notify himself/herself or people around the user of the user's state or transmit a predetermined signal to a family member, a guardian, or a designated place of an emergency medical center, when notifying a user or a designated place of a user's state.

The stroke monitoring system may further include: a psychological analysis unit configured to analyze a biometric signal measured by the measurement unit 200 to check a user's psychological state and stores the checked psychological state in the database 100, wherein the stroke determination unit 300 may use user's psychological information stored in the psychological analysis unit.

Other features and aspects will be apparent from the following detailed description, the drawings, and the claims.

[Detailed Description of Main Elements]

1: User
10: Bedroom
20: Residential space excluding bedroom
30: Playground
40: Car
100: Database
200: Measurement unit
210: Smart band    220: Electrocardiogram electrode
230: Electroencephalogram electrode    240: Motion sensing device
300: Stroke determination unit
400: Notification unit
500: Stroke history storage unit

DETAILED DESCRIPTION OF EMBODIMENTS

Hereinafter, a stroke monitoring system according to an embodiment of the present invention will be described in detail with reference to the accompanying drawings.

Figure 1:
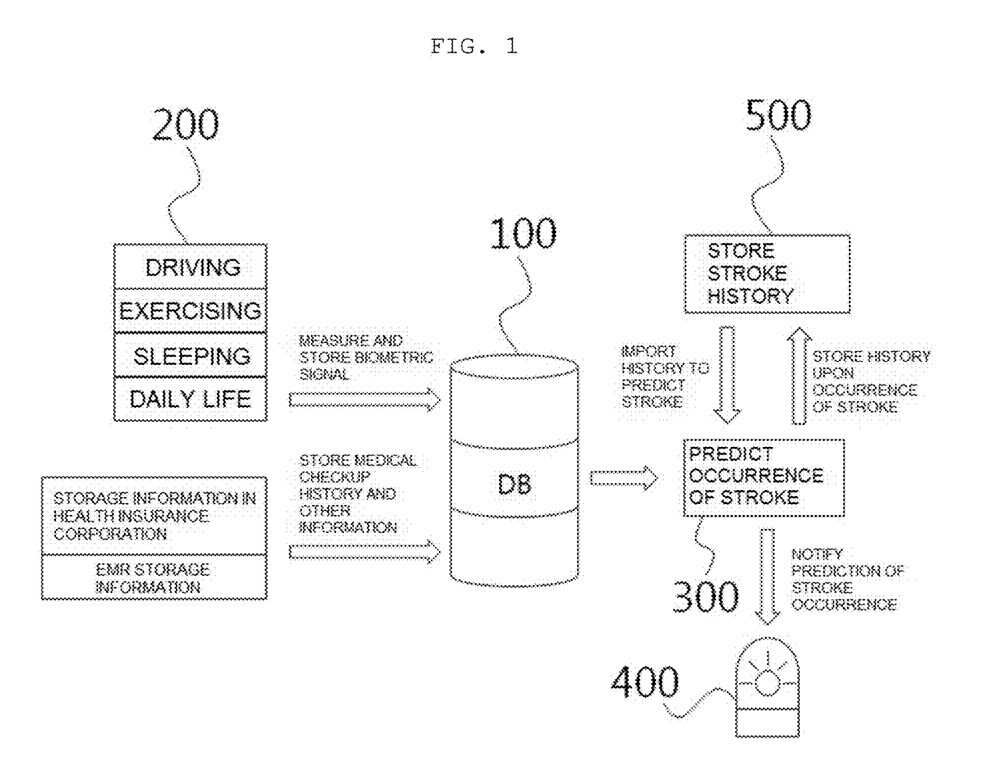
FIG. 1 is a block diagram according to one embodiment of the present invention.

FIG. 1 schematically shows a stroke monitoring system according to an embodiment of the present invention. As shown in FIG. 1, the stroke monitoring system according to an embodiment of the present invention includes a database 100, a measurement unit 200, a stroke determination unit 300, a notification unit 400 and a stroke history storage unit 500.

The database 100 stores user's health information. The user's health information may be various. The representative example may include a medical checkup history, medical checkup information, and measured electroencephalogram information of a user.

The medical checkup history and information may be continuously received by an institution such as the health insurance corporation that manages individual medical checkup. The medical checkup history may include personal information such as a name and age of a user, a medical checkup date, and user's biometric information measured in the relevant medical checkup.

A user's measurement electroencephalogram (EMR) may correspond to the case of separately measuring an electroencephalogram because the user has a stroke history. The user's measurement electroencephalogram stored in the database 100 may be an electroencephalogram measurement history as well as brain wave information.

The health information of the user stored in the database 100 may include information such as a family history or past medical history as well as the medical checkup history, the medical checkup information and the user's measurement electroencephalogram.

As described above, the user's health information stored in the database 100 is used in calculating a reference range to determine whether the user's state is normal in the stroke determination unit 300, which will be described later.

The measurement unit 200 is attached to a user or installed in a specific place to measure a biometric signal including an electroencephalogram and stores the measured electroencephalogram in the database 100. That is, the user's biometric signal which is provided from the measurement unit 200 and stored in the database 100 is the user's biometric information measured in real time, and the health information pre-stored in the database 100 is the user's biometric information which is not measured in real time.

Measuring the electroencephalogram by the measurement unit 200 is to continuously measure the user's electroencephalogram and the user's state, that is, predict the occurrence of the stroke based on the measured electroencephalogram since the electroencephalogram is changed upon the occurrence of the stroke or when the occurrence of the stroke is predicted. As the method for determining whether the stroke occurs by measuring the user's electroencephalogram, there are a method for indirectly determining whether the stroke occurs based on only the motion of the users as described in the related art 1 and a method for directly determining whether the stroke occurs. Here, the direct method may more improve the reliability on the determination of the stroke than the indirect method.

The measurement unit 200 may measure other biometric signals of a user in addition to the electroencephalogram. An example of other biometric signals may include one or more selected from an electrocardiogram, an electromyogram, electrooculogram, a heart rate, a blood pressure, a body temperature, skin conductivity, and a movement of a body. Various kinds of biometric signals other than the electroencephalogram are not base data for directly predicting the stroke like the electroencephalogram, but it is possible to increase reliability by measuring various biometric signals together with the electroencephalogram and using the measured biometric signals for the stroke prediction.

The measurement unit 200 may be a wearable device or may be an electrode which is attached to the body to measure various biometric signals. The wearable device and the electrode are directly mounted on or attached to the user's body so that the user measures his/her biometric information. However, as another example, the measurement unit may be provided as a device installed around the user to measure the motion of the user's specific part. The detailed examples of the measurement unit 200 will be described later.

The measurement unit 200 measures different kinds of biometric signals according to the user's state. For this purpose, the user's state should be defined first. In the stroke monitoring system according to the embodiment of the present invention, the user's state may be classified into states in which the user is exercising, sleeping, driving, or is in other daily lives.

Figure 2:
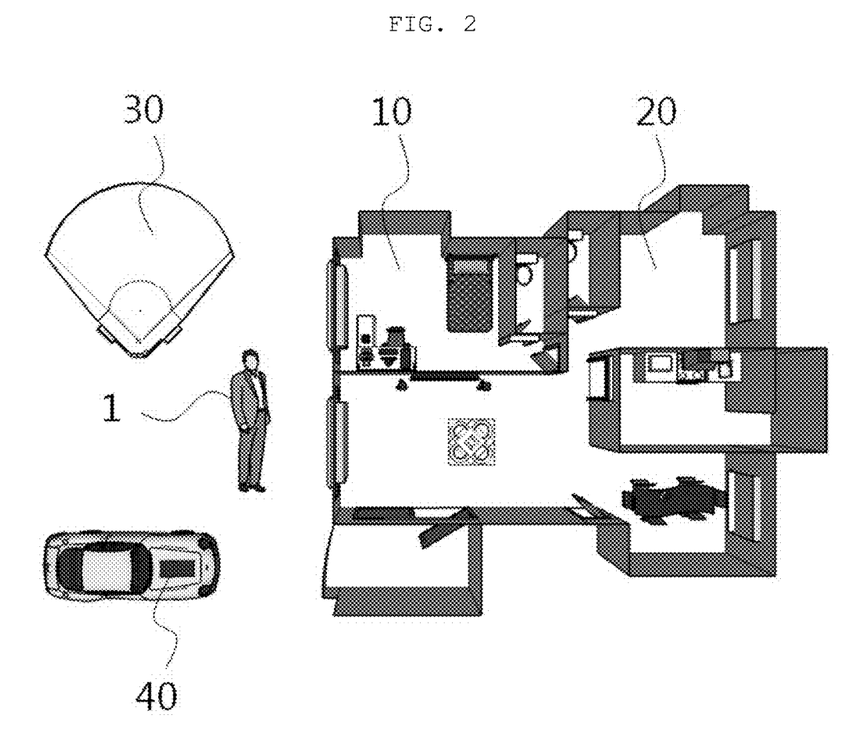
FIG. 2 is a schematic diagram illustrating a state of a user changing according to a location according to an embodiment of the present invention.

The measurement unit 200 may check user's state using various methods. FIG. 2 shows a schematic diagram of a method for using a signal device as an example of the method. According to the method, when the user's state is classified into exercising, sleeping, driving, or other daily life as described above, signal devices, which are separately installed in each space in which the exercising, the sleeping, the driving, or other daily life are made, communicate with the measurement unit 200 attached to or mounted on the user's body to notify the user's state. Referring to FIG. 2, first to fourth signal devices are installed in a bedroom 10, a residential space 20 excluding the bedroom, a playground 30, and a car 40, and if a user 1 goes to the corresponding space, the measurement unit 200 attached to the user 1 communicates with the closest signal device to check a space in which the user 1 is located, thereby measuring the state of the user 1.

For example, when the user 1 is sleeping, the first signal device installed in the bedroom 10 and the measurement unit 200 attached to the user 1 will communicate with each other, such that the measurement unit 200 may determine that the user's state is in the sleep state. The communicable coverage of the first signal device should be limited so as not to depart from the bedroom 10. In addition, a separate sensor is attached to a bed located inside the bedroom 10 to determine whether the user 1 is located on the bed. If the determined information interlocks with the first signal device, it is possible to more accurately check the state of the user 1.

When the user 1 is out of the bedroom 10, the first signal device and the measurement unit 200 cannot communicate with each other. Therefore, the measurement unit 200 may know that the user's state changes from the sleep state to the daily life based on the communication with the second signal device installed in the residential space 20 other than the bedroom.

In this way, the user's state may be checked by installing the third signal device on the playground 30 or installing the fourth signal device on the car 40. If the user is located in an area where the user may not communicate with a separate signal device, the measurement unit 200 may determine that the user is walking and determine that the user is in daily life. The reason why such a signal device can be used is that, in most cases, most of the users using the stroke monitoring system according to the embodiment of the present invention are old people with a stroke as their past medical history, and therefore a living space is limited to a certain range.

The method for using the signal device can automatically change the user's state without a separate manipulation. However, in addition to the method, the user may directly change his/her own state using a button on the measurement unit 200 or a remote controller.

The stroke determination unit 300 calculates the reference range of the user's biometric signal based on the health information pre-stored in the database 100 and compares and analyzes the biometric signal measured by the measurement unit 200 with the reference range, thereby predicting the occurrence of the user's stroke. As the method for using the pre-stored health information by the stroke determination unit 300, a method for averaging a range of bio-signals when the user is in a normal state through the medical checkup history and information included in the health information or a medical checkup method may be used. Alternatively, according to another method, a reference range may be determined to be a recommended range of a biometric signal of a primary care physician responsible for an examination in medical checkup information. The stroke determination unit 300 may notify the notification unit 400 when the user's biometric signal is out of or approaches the reference range, and the notification unit 400 can notify the user or the designated place of the fact. At this time, the notification unit 400 may notify different notification messages according to the proximity of the user's biometric signal to the reference range in the stroke determination unit 300. For example, if the measured blood pressure of the user approaches 80% of the maximum value of the reference range, the notification unit 400 may notify a "caution" stage, if the measured blood pressure approaches 90% of the maximum value of the reference range, the notification unit 400 may notify a "danger" stage, and if the measured blood pressure exceeds the maximum value of the reference range, the notification unit 400 may notify an "emergency" stage.

There are various methods of notifying, by the notification unit 400, the user's state to the user or the designated place. According to the embodiment of the present invention, a notification sound may be output so that a user may notify himself/herself or people around the user of his/her state or may transmit a predetermined signal to an emergency medical center or the designated place. The notification sound or the predetermined signal may be the "caution", "danger", or "emergency" stage messages output from the notification unit 400, and the user's biometric signals of the same time zone user may be transmitted or output together.

In the case of the notification sound output from the notification unit 400, an appropriate first aid method may be output for each stage. For example, when the user's state is "emergency", a CPR method may be output along with an "emergency" notification sound so that people around the user do a first aid like CPR. Also, the intensity of the notification sound output from the notification unit 400 may be differentially output according to the user's state. For example, the output value of the "caution" may be 60% of the maximum output value of the notification unit 400, the output value of the "danger" may be 80% of the maximum output value of the notification unit 400, and the output value of the "emergency" may be 100% of the maximum output value of the notification unit 400.

In order to transmit a location of a user from the notification unit 400 to a guardian, a family member, or an emergency medical center, a separate means for specifying the location of the user is required. For this purpose, the measurement unit 200 attached to the user's body or worn by the user may further include means for specifying the location of the user, such as a GPS.

The stroke history storage unit 500 stores the prediction history of the stroke determined by the stroke determination unit 300, and the stored stroke prediction history is provided to the stroke determination unit 300 to increase the accuracy of the prediction. That is, according to the embodiment of the present invention, when the history is stored in the stroke history storage unit 500 by performing fine-tuning which continuously updates the stroke history storage unit 500, the stroke determination unit 300 calculates the reference range based on the stroke history stored in the stroke history storage unit 500 and the health information of the user stored in the database 100 for stroke prediction, thereby more improving the prediction accuracy of the stroke.

The biometric signals of the user measured in real time in the measurement unit 200 and used for predicting the stroke occurrence are used in the stroke determination unit 300 and then are stored in the database 100 to be able to be used as the pre-stored health information. That is, the pre-stored health information of the user used when the stroke determination unit 300 predicts the stroke occurrence at the second point in time after the first point in time may be the user's biometric signals measured by the measurement unit 200 at the first point in time.

The stroke monitoring system according to the embodiment of the present invention may further include a psychological analysis unit. The psychological analysis unit analyzes the biometric signal measured by the measurement unit 200 to check a user's psychological state and stores the checked psychological state in the database 100. Recently, a variety of researches have been conducted to analyze the user's psychological state by using the measured biometric signals. As the representative example, in "A Study on Emotion Analysis Algorithm Using Electrocorticogram and Heart Variation" (Jun Gi Hwan and four persons, the Korean Computer Information Society, Vol 15 No. 10, 2010.10), the electroencephalogram and heart variation patterns are analyzed to be classified into emotions such as tranquility, concentration, tension, and depression. In addition, studies are being conducted to classify human emotions using other biometric signals such as skin conductivity. In embodiments of the present invention, the user's emotional state is analyzed using the user's biometric signal measured by the measurement unit 200, and the analyzed emotional state is stored in the database 100. The stroke determination unit 300 uses the user's emotional information to be able to predict the stroke. As a concrete example, if the psychological analysis unit determines that the current emotional state of the user is tension, the stroke determination unit 300 may reflect the current emotional state to broaden the reference range of some items of the user's biometric signals.

Hereinafter, the case in which the signals measured by the measurement unit 200 vary according to user's state will be described.

When the user's state is an exercise, the signal measurable by the measurement unit 200 may be an electroencephalogram (EEG), an electrocardiogram (ECG), an electromyogram (EMG), or a heart rate. The reason why the measurable signal is limited by the measurement unit 100 is due to the characteristics of the exercise. In other words, the reason why the measurable signal is limited by the measurement unit 100 is that it is difficult to measure the blood pressure during exercise and that since there are various types of exercises, it is difficult to measure whether the user has the stroke based on the movement of the body. However, in the case of types of exercises in which a direction of eyes or a face should be fixed during the exercise, the movement of the eyes and the face is measured by a separate means capable of measuring the movement of the eyes or the face during the movement of the body, thereby determining whether the user has the stroke.

Figure 3:
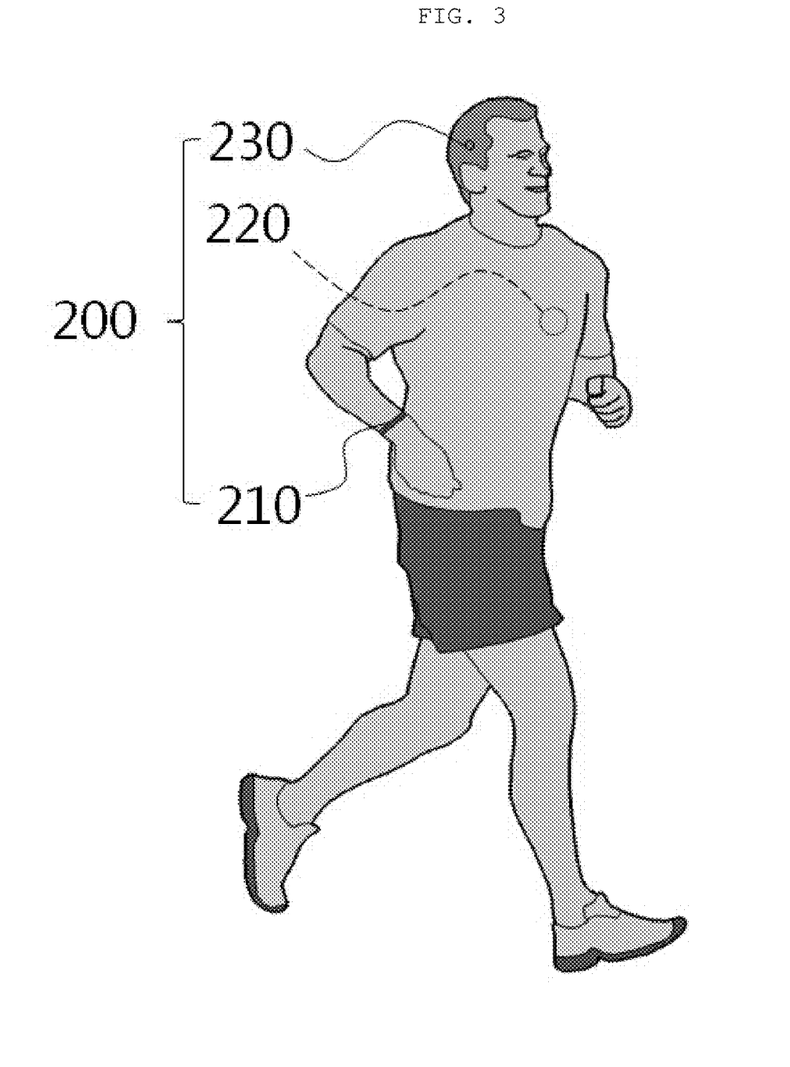
FIG. 3 is a diagram showing a state in which a user is exercising.

FIG. 3 shows a case in which the user jogs lightly. In this case, the user's heart rate, electrocardiogram (ECG), electroencephalogram (EEG) and skin conductivity can be measured. In FIG. 3, the measurement unit 200 which may be attached to the user may be a smart band 210, an electrocardiogram electrode 220, and an electroencephalogram electrode 230.

Figure 4:
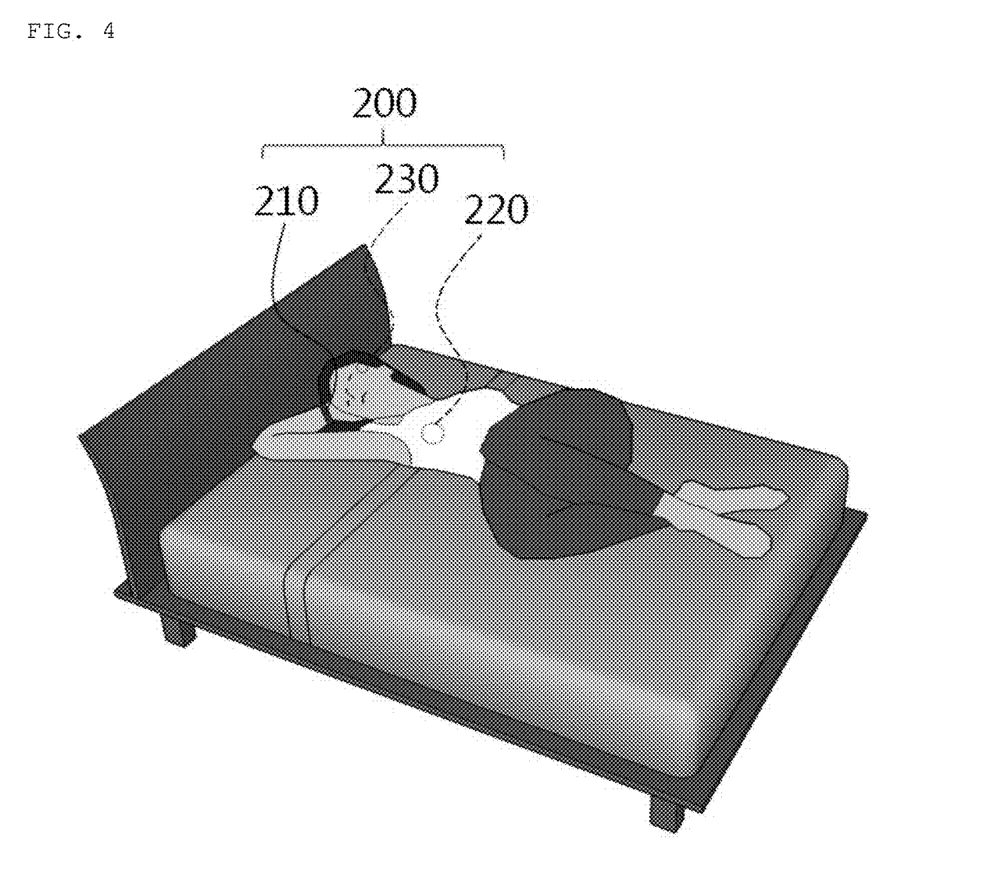
FIG. 4 is a diagram showing a state in which a user is in one's sleep.

FIG. 4 illustrates a case in which the user is sleeping. In this case, the electroencephalogram, the electrocardiogram, the electromyogram, the heart rate, the electrooculogram, the skin conductivity, and the blood pressure may be measured through the smart band 210, the electrocardiogram electrode 220, and the electroencephalogram electrode 230 attached to the user. In the case of the electrooculogram, a separate electrode is attached to the face to measure the movement of an eyeball by measuring the potential difference between the front and back of the eyeball. Through the measured electrooculogram, it is possible to know whether the user is deeply or shallowly asleep and whether the stroke occurs. More specifically, in case of general people, the REM sleep and non-REM sleep are periodically observed. When the stroke occurs, the REM and non-REM sleep that are observed periodically do not appear periodically and may be instantaneously changed to the REM sleep, such that it is possible to determine whether the stroke occurs. In the case of the smart band 210, since it is mounted on the wrist, the movement of the user is measured using a sensor that senses the movement of the smart band 210 itself, such as a motion sensor and a gyroscope included therein, which can be utilized for the prediction of the stroke occurrence.

Figure 5:
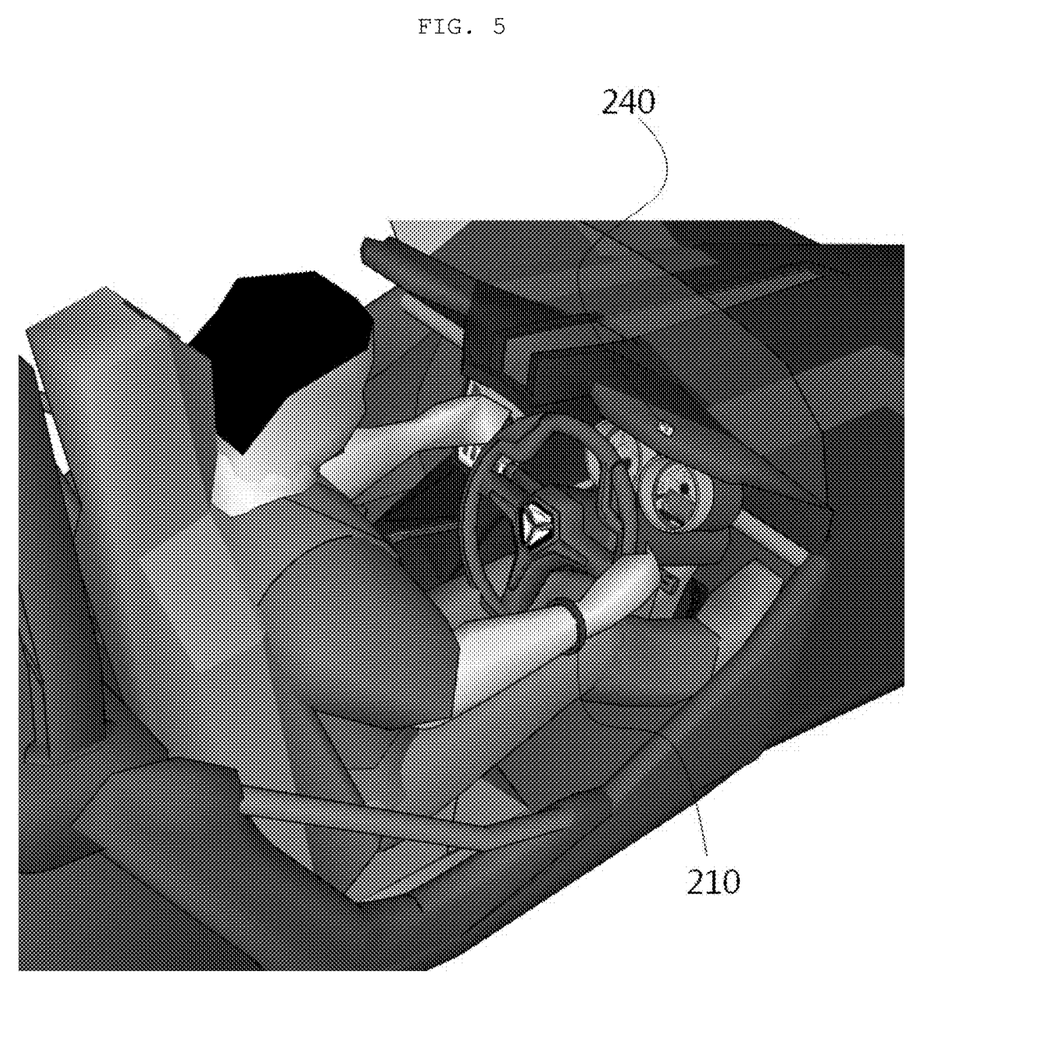
FIG. 5 is a diagram showing a state in which a user is driving.

FIG. 5 shows a case in which the user is driving. In this case, the smart band 210, the electrocardiogram electrode, and the electroencephalogram electrode attached to the user and a motion sensing device 240 additionally installed in a vehicle measure the electroencephalogram, the electrocardiogram, the electromyogram, the heart rate, the blood pressure, and the movement of the body, which may be utilized for the prediction of the stroke occurrence of the user.

Figure 6:
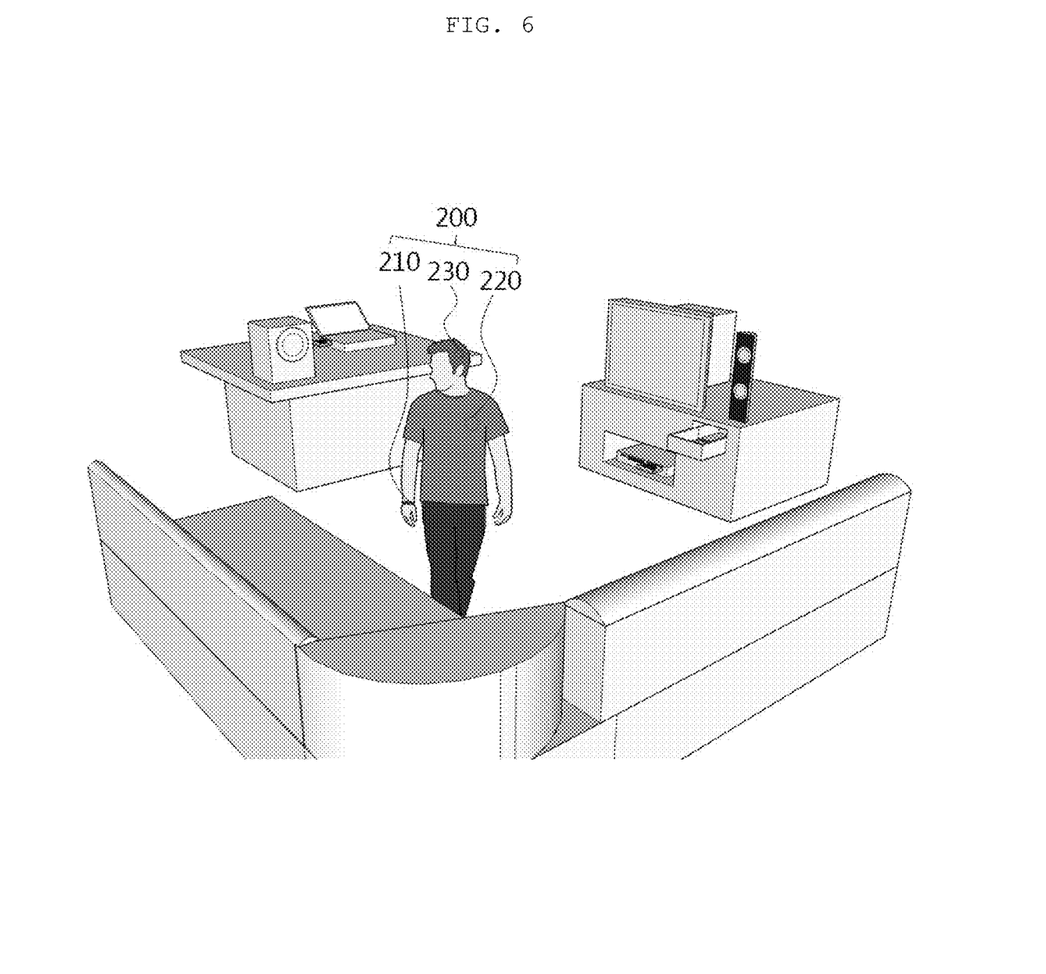
FIG. 6 is a diagram showing a state in which a user is in one's daily life.

FIG. 6 shows a case in which the user's state is in daily life except the state in which the user is exercising, sleeping, and driving. In this case, the types of measurable biometric signals may include the electroencephalogram, the electrocardiogram, the electromyogram, the heart rate, the skin conductivity, and the blood pressure.

When the stroke monitoring system according to the embodiment of the present invention is performed, the database 100 stores various information of the user including the measured biometric signals of the user. The stroke monitoring system according to the embodiment of the present invention may further include the classification unit (not shown) that classifies such information into items, and visualizes and provides these items. The classification unit classifies and provides the information stored in the database 100 according to date, time, area, and biometric signal by the user's operation.

Hereinabove, the case in which the stroke monitoring system according to the embodiment of the present invention is applied to a single user is described. However, the stroke monitoring system according to the embodiment of the present invention can be applied to a single user. In addition to this, the information stored in an individual user's database 100 may be gathered to form the upper database. Accordingly, the central government, local governments, and enterprises use the database to carry out the stroke related policies or manage the health of stroke patients.

According to the stroke monitoring system according to embodiments of the present invention as described above, it is possible to predict the occurrence of the user's stroke throughout the daily life of the user and notify a user, people around the user, or nearby hospitals of the occurrence of the user's stroke, thereby preventing the user's stroke from occurring and performing the quick first aid upon the occurrence of the stroke.

According to the embodiment of the present invention, since the prediction of the occurrence of the stroke is synthetically determined using the user's biometric signal, the medical checkup history, and the predicted psychological state, the reliability on the determination on whether the stroke occurs and the occurrence prediction of the stroke can be improved.

The present invention is not limited to the above-mentioned embodiments, and may be variously applied, and may be variously modified without departing from the gist of the present invention claimed in the claims.

What is claimed is:

1. A stroke monitoring system, comprising:
a database configured to store user's health information;
a measurement unit configured to be worn by a user or installed in a specific place to measure a biometric signal and store the measured biometric signal in the database;
a stroke determination unit configured to calculate a reference range of the user's biometric signal based on the health information pre-stored in the database and further configured to compare and analyze the biometric signal measured by the measurement unit with the reference range to predict a chance for occurrence of a stroke in the user;
a notification unit configured to notify the user or a designated place of the prediction by the stroke determination unit;
a stroke history storage unit configured to store the prediction by the stroke determination unit; and a signal device installed in a user living space selected from the group consisting of an exercising space for exercising, a sleeping space for sleeping, and a driving space for driving a vehicle, wherein the measurement unit is configured to wirelessly communicate with the signal device when the measurement unit is located within a communicable range from the signal device, wherein the measurement unit is further configured to identify which living space the signal device is installed to detect a state of the user selected from the group consisting of an exercising state, a sleeping state, and a driving state, wherein, when the user is in the exercising state, the measurement unit is configured to measure the biometric signal comprising an electroencephalogram, an electrocardiogram, a heart rate, and a skin conductivity, wherein, when the user is in the sleeping state, the measurement unit is configured to measure the biometric signal comprising the electroencephalogram, the electrocardiogram, the heart rate, the skin conductivity, an electrooculogram, an electromyogram, and a blood pressure, wherein, when the user is in the driving state, the measurement unit is configured to measure the biometric signal comprising the electroencephalogram, the electrocardiogram, the heart rate, the electromyogram, and the blood pressure, wherein the stroke determination unit is configured to calculate the reference range that changes depending on the user's state detected by the measurement unit, wherein the stroke determination unit is configured to compare and analyze the biometric signal measured by the measurement unit with the reference range specifically calculated for the user's state to predict the chance of occurrence of the stroke.

2. The stroke monitoring system of claim 1, wherein the stroke determination unit is configured to calculate the reference range based on the user's health information stored in the database and further based on prior predictions stored in the stroke history storage unit.

3. The stroke monitoring system of claim 1, wherein the user's health information includes a medical checkup history, medical checkup information, and user's measurement electroencephalogram information.

4. The stroke monitoring system of claim 1, wherein the notification unit is configured to output a notification sound to the user or people around the user or configured to transmit a predetermined signal to a family member, a guardian, or an emergency medical center, when notifying the user or the designated place of the prediction.

5. The stroke monitoring system of claim 1, further comprising:

a psychological analysis unit configured to analyze the biometric signal measured by the measurement unit to check a psychological state of the user and store the checked psychological state in the database, wherein the stroke determination unit is configured to use the user's psychological information stored in the psychological analysis unit when predicting the chance for occurrence of the stroke.

* * * * *